(12) United States Patent
Yamada

(10) Patent No.: US 7,066,009 B2
(45) Date of Patent: Jun. 27, 2006

(54) GAS SENSOR

(75) Inventor: Hirokazu Yamada, Nagoya (JP)

(73) Assignee: Denso Corporation, Kariya (JP)

( * ) Notice: Subject to any disclaimer, the term of this patent is extended or adjusted under 35 U.S.C. 154(b) by 98 days.

(21) Appl. No.: 10/859,110

(22) Filed: Jun. 3, 2004

(65) Prior Publication Data
US 2004/0244467 A1 Dec. 9, 2004

(30) Foreign Application Priority Data

Jun. 6, 2003 (JP) ............................. 2003-162511
Apr. 6, 2004 (JP) ............................. 2004-112419

(51) Int. Cl.
*G01N 7/12* (2006.01)
(52) U.S. Cl. ..................... 73/31.05; 73/23.31; 73/23.32
(58) Field of Classification Search ............... 73/23.31, 73/23.32, 23.33, 31.05, 31.06; 204/424, 204/425, 427, 428, 431, 432, 434, 435
See application file for complete search history.

(56) References Cited

U.S. PATENT DOCUMENTS

| 4,011,655 | A | * | 3/1977 | Beaudoin et al. ............. 29/612 |
| 4,283,261 | A | * | 8/1981 | Maurer et al. ............... 204/408 |
| 6,477,887 | B1 | | 11/2002 | Ozawa et al. |
| 6,497,808 | B1 | * | 12/2002 | Yamauchi et al. ........... 205/785 |
| 2002/0000033 | A1 | * | 1/2002 | Tajima et al. ............... 29/592.1 |

FOREIGN PATENT DOCUMENTS

| JP | 09229899 A | * | 9/1997 |
| JP | 10-206373 | | 8/1998 |
| JP | 2001-188060 | | 7/2001 |

* cited by examiner

*Primary Examiner*—Charles Garber
(74) *Attorney, Agent, or Firm*—Nixon & Vanderhye P.C.

(57) ABSTRACT

In a gas sensor internally including a sensing element for measuring a specific gas concentration of a measured gas, an outer surface thereof has a measured gas surface exposed to a measured gas and an atmosphere surface exposed to the atmosphere, and at least a portion of the atmosphere surface has an emissivity equal to or lower than 0.3. Preferably, this emissivity is a value with respect to an electromagnetic wave having a wavelength of 0.5 to 1 μm, and the a region of the atmosphere surface, contributing 60% or more of the atmosphere surface, has an emissivity equal to or lower than 0.3. This provides a gas sensor less susceptible to radiant heat and less temperature-increasable.

8 Claims, 4 Drawing Sheets

GAS SENSOR

BACKGROUND OF THE INVENTION

1) Field of the Invention

The present invention relates to a gas sensor made to measure an oxygen concentration or the like in an exhaust gas from an engine for a vehicle for the purpose of utilizing the measurement result for the combustion control or the like.

2) Description of the Related Art

The combustion control based on the oxygen concentration or the like in the exhaust gas from a vehicle engine works effectively for the fuel consumption and the efficient exhaust gas purification.

A gas sensor for detecting the oxygen concentration or the like in the exhaust gas internally includes a sensing element for measuring a specific gas concentration of a measured gas (gas to be measured).

This gas sensing element has an electrochemical cell comprising a solid electrolyte and a pair of electrodes and is made to measure an oxygen concentration or the like in a measured gas on the basis of an electromotive force occurring between the electrodes, a limiting current flowing therebetween, or the like with the atmospheric gas being used as a reference gas.

Accordingly, there is a need for the gas sensor to come into contact with both the atmosphere and measured gas, and an outer surface of the gas sensor includes a measured gas surface exposed to the measured gas and an atmosphere surface exposed to the atmosphere. The measured gas surface has an introduction hole for introducing the measured gas into the interior of the gas sensor while the atmosphere surface has an introduction hole for introducing the atmosphere into the interior of the gas sensor.

For example, in the case of a gas sensor shown in FIG. 1 and described later, the gas sensor is inserted into a mounting hole made in an exhaust pipe in which an exhaust gas flows, and a housing is divided halfway so that one division forms an atmosphere surface and the other forms a measured gas surface.

Meanwhile, of the components of a gas sensor, there are materials inferior in thermal resistance. For example, a resin-made water repelling filter (see FIG. 1 and others) is sometimes provided for making the introduction of the atmosphere into the interior of an atmospheric side cover possible but the intrusion of water thereinto preventable. This water repelling filter is made of a porous resin material such as tetrafluoroethylene and its thermal resistance falls below that of a metal or ceramic material.

In addition, an elastic insulating material (see FIG. 1 and others) is sometimes provided for hermetically sealing a base end portion of an atmospheric side cover and for fixing lead wires drawn from the exterior of the gas sensor. However, this elastic insulating material is made of a resin or a rubber and is inferior in thermal resistance.

Furthermore, in recent years, the regulation on the exhaust gas becomes stricter every year and, with this situation, the temperature of the exhaust gas further increases and an outer surface of an exhaust pipe heated by the hot exhaust gas glows, thereby further generating radiant heat.

Since the atmosphere surface of the outer surface of the gas sensor is exposed to the exterior of the exhaust pipe, it can become a radiant heat receiving surface. The radiant heat promotes heating the gas sensor so that there is a possibility of exceeding the thermal resistance limit of a material sensitive to (weak in) heat.

There have been proposed a construction in which an outer surface of the base end of the atmospheric side cover is formed into irregular configuration to form a heat radiating portion or the size of a gas sensor is increased to lengthen the distance between the exhaust pipe and the outer surface for preventing the temperature of the gas sensor from increasing excessively.

However, it is preferable that the gas sensor to be placed in a limited space is made as smaller as possible, and the size enlargement is not desirable also from the viewpoint of the material cost. Moreover, difficulty is experienced in manufacturing the outer surface having the irregular configuration, which leads to lowering the productivity.

SUMMARY OF THE INVENTION

The present invention has been developed in order to eliminate the above-mentioned conventional problems, and it is therefore an object of the invention to provide a gas sensor less susceptible to the radiant heat from the external and less temperature-increasable.

For this purpose, in accordance with a first aspect of the present invention, there is provided a gas sensor internally including a sensing element for measuring a specific gas concentration in a measured gas to be measured wherein an outer surface of the gas sensor includes a measured gas surface exposed to the measured gas and an atmosphere surface exposed to the atmosphere, and at least a portion of the atmosphere surface has an emissivity equal to or lower than 0.3.

In the gas sensor according to the present invention, a region of the emissivity being equal to or lower than 0.3 is provided on the atmosphere surface, thereby reducing the heat transmission stemming from the radiant heat with respect to the atmosphere surface so that the temperature of the gas sensor becomes less raisable. Moreover, since this can block the heat transmission to the atmosphere surface, the temperature in the vicinity of the atmosphere surface becomes less increasable.

Therefore, the present invention can provide a gas sensor less susceptible to the radiant heat from the external and less temperature-increasable.

BRIEF DESCRIPTION OF THE DRAWINGS

Other objects and features of the present invention will become more readily apparent from the following detailed description of the preferred embodiments taken in conjunction with the accompanying drawings in which.

DESCRIPTION OF THE PREFERRED EMBODIMENTS

Figure 1:
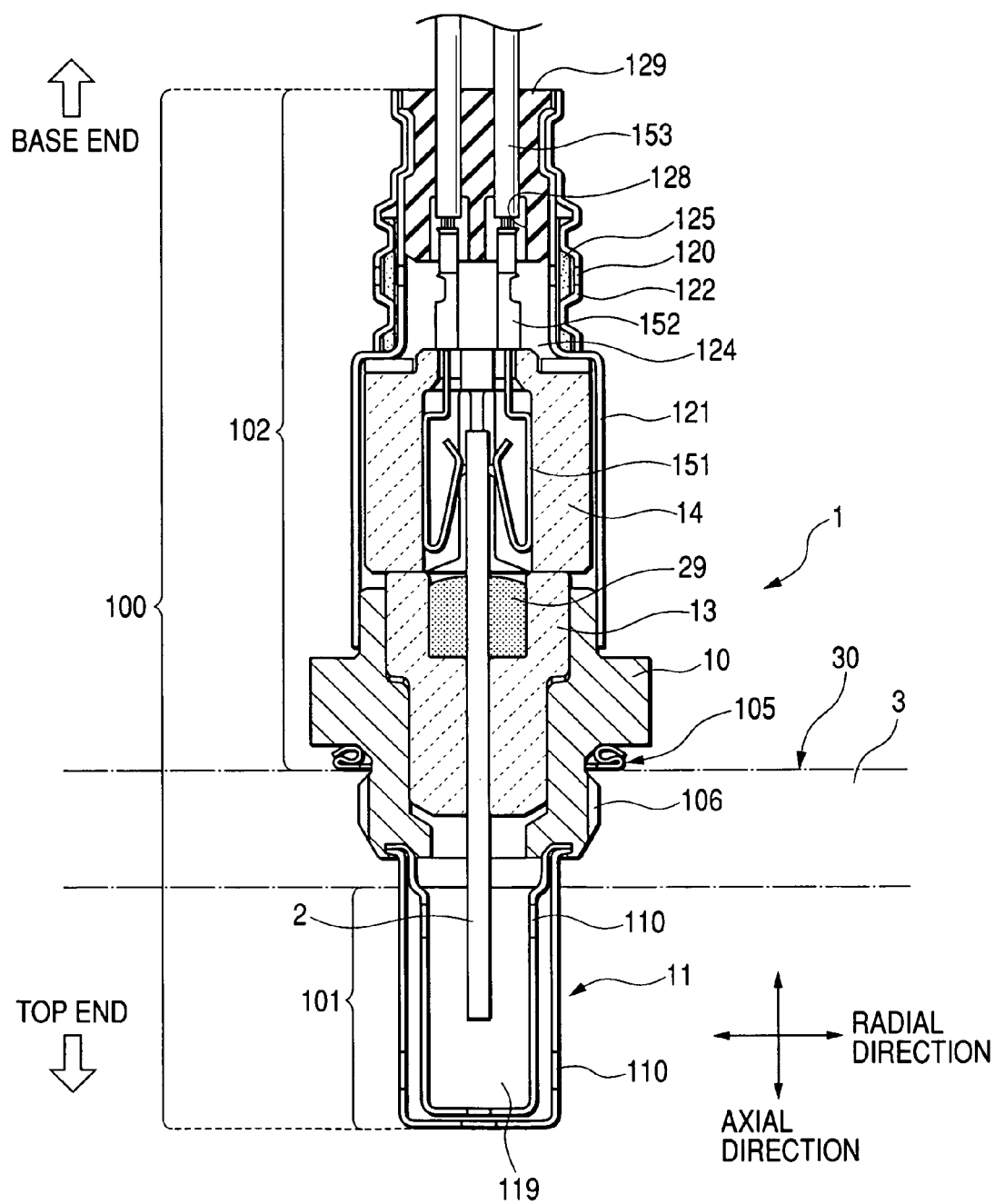
FIG. 1 is an axially cross-sectional view showing a gas sensor according to a first embodiment of the present invention.

The present invention is applicable various types of gas sensors, such as oxygen sensor, NOx sensor, other gas sensors, an air-fuel ratio sensor made to measure an air-fuel ratio in an combustion chamber of a vehicle engine on the basis of an oxygen concentration in an exhaust gas, and others.

The sensing element 2 may be implemented by either of a laminate type and a cup-shaped type, as are well known in the art.

Although a detailed construction of a gas sensor will be described later, the effects of the present invention are also obtainable also in the case of gas sensors other than those described in the embodiments.

In a case in which a region (range) whose emissivity is equal to or lower than 0.3 does not exist in the atmosphere surface, the heating of the gas sensor is enhanced due to the radiant heat so that there is a possibility of exceeding the thermal resistance limit of a material sensitive to heat.

In this case, of the components of the gas sensor, the "material sensitive to heat" signifies materials each made of resin, rubber or the like, for example, water repelling filters, elastic insulating members equipped with a lead wire insertion hole and provided at a base end portion of an atmosphere side cover, and others (see first embodiment).

The emissivity can be set at zero. In this case, all the heat from the external is reflected so that the gas sensor becomes extremely less subject to heat, thereby further suppressing the increase in temperature.

Furthermore, it is preferable that the emissivity of at least a portion of the aforesaid atmosphere surface is equal to or lower than 0.15.

When the emissivity is set at values equal to or lower than 0.15, the heat transmission due to the radiant heat with respect to the atmosphere surface becomes further reduced so that the temperature becomes less increasable.

Still furthermore, preferably, the aforesaid emissivity is a value with respect to an electromagnetic wave having a wavelength of 0.5 to 1 μm.

In this case, the reflection of the radiation becomes feasible in a visible light region and in an infrared region. The wavelength of the electromagnetic wave generated when a metallic material such as an exhaust pipe glows is approximately between that of the visible light and that of the infrared light, and if the reflection of the electromagnetic wave with this wavelength is possible, sufficient effects are attainable in terms of the suppression of temperature rise of the gas sensor.

Yet furthermore, preferably, the atmosphere surface is made from a shot-blast-treated surface.

The shot blast treatment can remove an oxide film and others formed on a face of the atmosphere surface so that the metallic shiny appears. Therefore, a low emissivity is obtainable.

For the aforesaid shot blast, it is preferable to use a fine powder of glass, ceramics or the like as an abrasive. Moreover, in the gas sensor according to the present invention, the atmosphere surface is made of an atmospheric side cover and others, or a housing and others.

That is, in general, as described later in the first embodiment, the gas sensor is made up of a housing, a measured gas side cover provided on the top end of the housing and an atmospheric side cover provided on the base end of the housing. Cover members other than the atmospheric side cover and the measured gas side cover can be exposed in the outer surface.

The interior of each of the atmospheric side cover and the measured gas side cover comes into an atmospheric ambiance or measured gas environment, and the sensing element internally included in the gas sensor is disposed to span (straddle the border between) both the atmospheric ambiance and measured gas environment.

In this construction, preferably, a passive-state film (oxide film) is formed on the entire atmospheric side cover in advance and a needed region is shot-blast-treated to form a shot-blast-treated surface.

That is, in the gas sensor, since the sensing element is made to carry out the detection with the atmospheric ambiance being used as a reference gas, when a metallic member, such as the atmospheric side cover, constituting the gas sensor oxidizes under a high-temperature environment, the oxygen concentration of the atmospheric ambiance lowers so that the detection value gets out of order.

Accordingly, in general, a strong passive-state film (oxide film) is formed on the surface of the atmospheric side cover or the like by heating it up to a high temperature in advance, thus preventing the oxidization from accelerating under a high-temperature environment in use. Through his treatment, the atmospheric side cover has an oxidized surface with brown to dark brown shiny and its emissivity tends to be high. Therefore, the easiest manufacturing method for obtaining a low emissivity according to the present invention is the shot blast treatment.

As other methods, the grinding and acid treatment are also acceptable for removing the passive-state film.

Moreover, preferably, the emissivity of a region occupying 60% or more of the atmosphere surface is equal to or lower than 0.3.

This reduces the heat transmission due to the radiant heat with respect to the atmosphere surface so that the temperature of the gas sensor becomes less increasable. In addition, the hindrance of the heat transmission to the atmosphere surface prevents the temperature of the atmosphere surface from rising.

Assuming that a region in which the emissivity is equal to or lower than 0.3 does not reach 60%, there is a possibility of the effects on the suppression of the temperature rise of the gas sensor being insufficient.

Most preferably, the entire atmosphere surface has an emissivity equal to or lower than 0.3.

Still moreover, preferably, when the distance from the base end portion of the atmosphere surface to the top portion thereof along an axial direction of the gas sensor is taken as H, the emissivity is set at 0.3 or less in a region corresponding to (having) a distance of 0.6H or more from the base end portion thereof toward the top portion along the axial direction of the gas sensor.

In a case in which the gas sensor is used in a state inserted into an exhaust pipe of a vehicle engine to be exposed to the exhaust gas, the exhaust pipe is heated by the hot exhaust gas and glows to generate the radiant heat. Moreover, in the case of most gas sensors, as mentioned later in the first embodiment, members such as resins or rubbers sensitive to heat are positioned at the base end of the gas sensor. Therefore, when portions whose emissivity is low is provided at the base end, it is possible to particularly suppress the temperature rise in the vicinity of the base end.

If the region in which emissivity is equal to or lower than 0.3 has a distance below 0.6H, there is a possibility that the effects on the suppression of the temperature rise of the base end of the gas sensor becomes particularly insufficient.

First Embodiment

Figure 2:
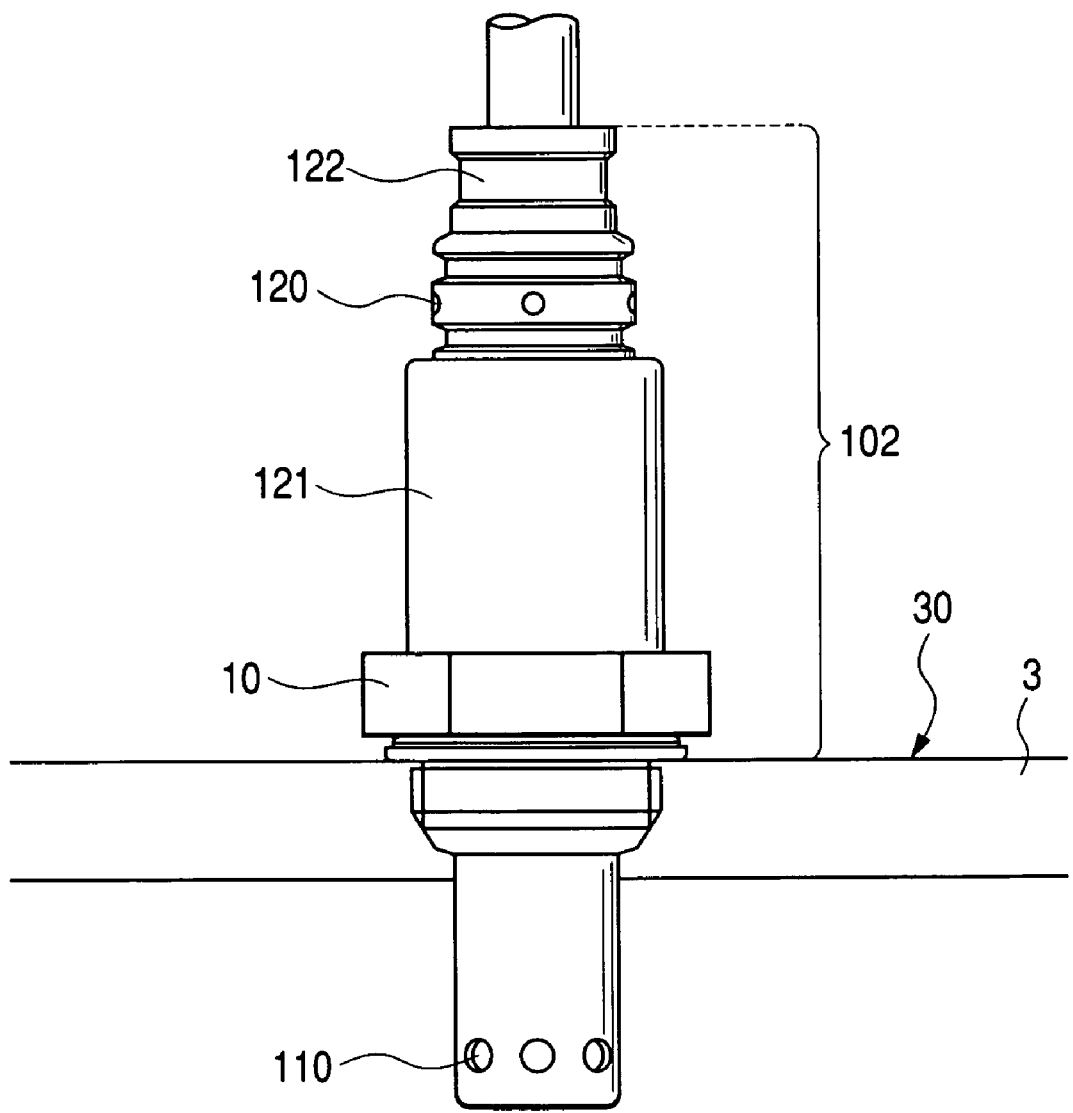
FIG. 2 is a side elevational view showing the gas sensor according to the first embodiment.

As shown in FIGS. 1 and 2, a gas sensor according to this embodiment, generally designated at reference numeral 1, internally includes a sensing element 2 for measuring a specific gas concentration in a measured gas, and an outer surface 100 of the gas sensor 1 has a measured gas surface 101 exposed to a measured gas and an atmosphere surface 102 exposed to the atmosphere. The emissivity of at least a portion of the atmosphere surface 102 is equal to or lower than 0.3.

A detailed description will be given hereinbelow of the gas sensor 1 according to this embodiment.

As FIG. 1 shows, the gas sensor 1 according to this embodiment is made such that a housing 10 is threadly fixed to a screw portion of a gas sensor fixing hole made in an exhaust pipe 3 of a vehicle engine and a portion of the top end of the gas sensor 1 is exposed to the exhaust gas to measure an air-fuel ratio in a combustion chamber (not shown) of the vehicle engine on the basis of an oxygen concentration of the exhaust gas.

According to this embodiment, although not shown, the sensing element 2 is made such that a pair of electrodes are provided on a plate-like solid electrolyte member and one electrode comes into contact with a measured gas environment 119 while the other electrode comes into contact with an atmospheric ambiance 124. An oxygen concentration of an exhaust gas producing the measured gas environment 119 is detectable with the atmospheric ambiance 124 in the interior of the gas sensor 1 being used as a reference gas.

As FIG. 1 shows, the gas sensor 1 according to this embodiment is made up of the cylindrical housing 10 and the sensing element 2 inserted through a device side insulator 13 into an inner surface of the housing 10.

A hermetic sealing material 29 is placed between the sensing element 2 and the device side insulator 13 to inhibit the flow of a gas. This sealing material 29 forms a boundary between the atmospheric ambiance 124 and the measured gas environment 119.

On the top end of the housing 10, a measured gas side cover 11 with a double structure is provided so as to cover a gas concentration detecting portion of the top end of the sensing element 2. The measured gas side cover 11 has an introduction hole 110 whereby a measured gas is introduced from the exterior of the gas sensor 1 into the interior of the cover 11. The interior of the cover 11 forms the measured gas environment 119.

In addition, on the base end of the element side insulator 13, a cylindrical atmospheric side insulator 14 is provided so as to cover the base end of the sensing element 2, and an atmospheric side cover 121 is fixedly welded to the base end of the housing 10 so as to cover the outside of the atmospheric side insulator 14.

An outer cover 122 is provided through a cylindrical water repelling filter 125 on an outer circumference of the base end of the atmospheric side cover 121 and fixedly caulked from the outside of the outer cover 122, thereby fixing the water repelling filter 125. At the position of the water repelling filter 125, an introduction hole 120 is made in the atmospheric side cover 121 and the outer cover 122 to introduce the atmosphere into the interior of the atmospheric side cover 121. The interior of the atmospheric side cover 121 forms the atmospheric ambiance 124. The base end of the atmospheric side cover 121 is hermetically sealed by an elastic insulating member 129 which will be mentioned later.

In the interior of the atmospheric side insulator 14, an output fetching/power applying terminal (not shown) and a terminal spring 151 come into contact with each other, and the base end of the terminal spring 151 located in the exterior of the atmospheric side insulator 14 where it is connected through a connecting terminal 152 to a lead wire 153. The lead wire 153 is drawn to the exterior of the sensor 1 through a lead wire insertion hole 128 which is a through hole made in an elastic insulating member 129 placed in the interior of the base end of the atmospheric side cover 151.

Each of the atmospheric side cover 121 and the outer cover 122 is made of a stainless material having, on its surface, a passive-state film (oxide film) formed by heating it up to a high temperature. As the stainless material, there is used an austenite-based SUS310 or SUS316 having a thermal resisting property.

That is, in the gas sensor 1, since the sensing element 2 makes the detection in a manner such that the atmospheric ambiance 124 in the gas sensor 1 is used as the reference gas, when the metal members such as the atmospheric side cover 121, constituting the gas sensor 1, oxidize under a high-temperature environment, the oxygen concentration of the atmospheric ambiance 124 lowers so that difficulty is encountered in obtaining a detection value accurately.

For this reason, the atmospheric side cover 121 and others are heated at a high temperature in advance to form a strong passive-state film (oxide film) on their surfaces for preventing the oxidization from accelerating under a high-temperature environment in use. Through this treatment, the atmospheric side cover 121 and other come into an oxidized surface state having brown to dark brown shiny.

In this embodiment, the shot blast is used for the atmospheric side cover 121 and the outer cover 122 so that a passive-state film corresponding to the atmosphere surface 102 is removed to make the stainless produce metallic shiny. Thus, the emissivity becomes 0.3 or less.

For the aforesaid shot blast, a fine powder of glass, ceramics or the like is used as an abrasive.

The housing 10 is made such that its top end portion has a small diameter, its intermediate portion has a large diameter and its base end portion has a small diameter, and is equipped with a spring portion 105 on a lower surface of the large-diameter intermediate portion. A side surface of the small-diameter top end portion has a screw portion 106 corresponding to the screw portion of the gas sensor fixing hole of the exhaust pipe 3.

When the housing 10 of the gas sensor 1 is threadly set in the exhaust pipe 3, a surface of the spring portion 105 facing the top end is brought into contact with a surface 30 of the exhaust pipe 3.

Moreover, of the outer surface 100 of the gas sensor 1, a surface of the measured gas side cover 11 exposed in the interior of the exhaust pipe 3 forms the measured gas surface 101, while a side surface of the base end of the housing, a side surface of the atmospheric side cover 121 and a side surface of the outer cover 122 form the atmosphere surface 102.

Incidentally, in FIG. 1 or 2, the existence ranges of the outer surface 100, the measured gas surface 101 and the atmosphere surface 102 are indicated by arrow lines.

In the gas sensor 1 according to this embodiment, the atmosphere surface 102 is made such that its emissivity is set at 0.3 or less, which reduces the heat transmission due to the radiant heat with respect to the atmosphere surface 102 and makes the temperature of the gas sensor 1 less raisable. Moreover, since this can block the heat transmission to the atmosphere surface 102, the temperature in the vicinity of the atmosphere surface becomes less increasable.

In the gas sensor 1 according to this embodiment, the water repelling filter 125 is made of tetrafluoroethylene and the elastic insulating member 129 is made of fluoro rubber.

The maximum temperature of the exhaust gas flowing in the interior of the exhaust pipe 3 is approximately 800° C.

and, hence, the surface 30 of the exhaust pipe 3 is also heated to about this temperature and glows to generate an electromagnetic wave, i.e., infrared or visible light.

Assuming that the formed passive-state film remains on the surfaces of the atmospheric side over 121 and others, the temperature rise in the gas sensor 1 is unavoidable as mentioned later in the second embodiment, and the heat deterioration can occur in the water repelling filter 125 or the elastic insulating member 129.

In this embodiment, since the atmosphere surface 102 of the atmospheric side cover 121 and others is treated through the use of the shot blast, the stainless metallic shiny appears and the emissivity becomes equal to or lower than 0.3. As mentioned later in the second embodiment, the temperature of the gas sensor 1 becomes less increasable and the heat deterioration of the water repelling filter 125 or the elastic insulating member 129 becomes preventable.

As described above, according to this embodiment, it is possible to provide a gas sensor less susceptible to the radiant heat from the external and less temperature-increasable.

Figure 3:
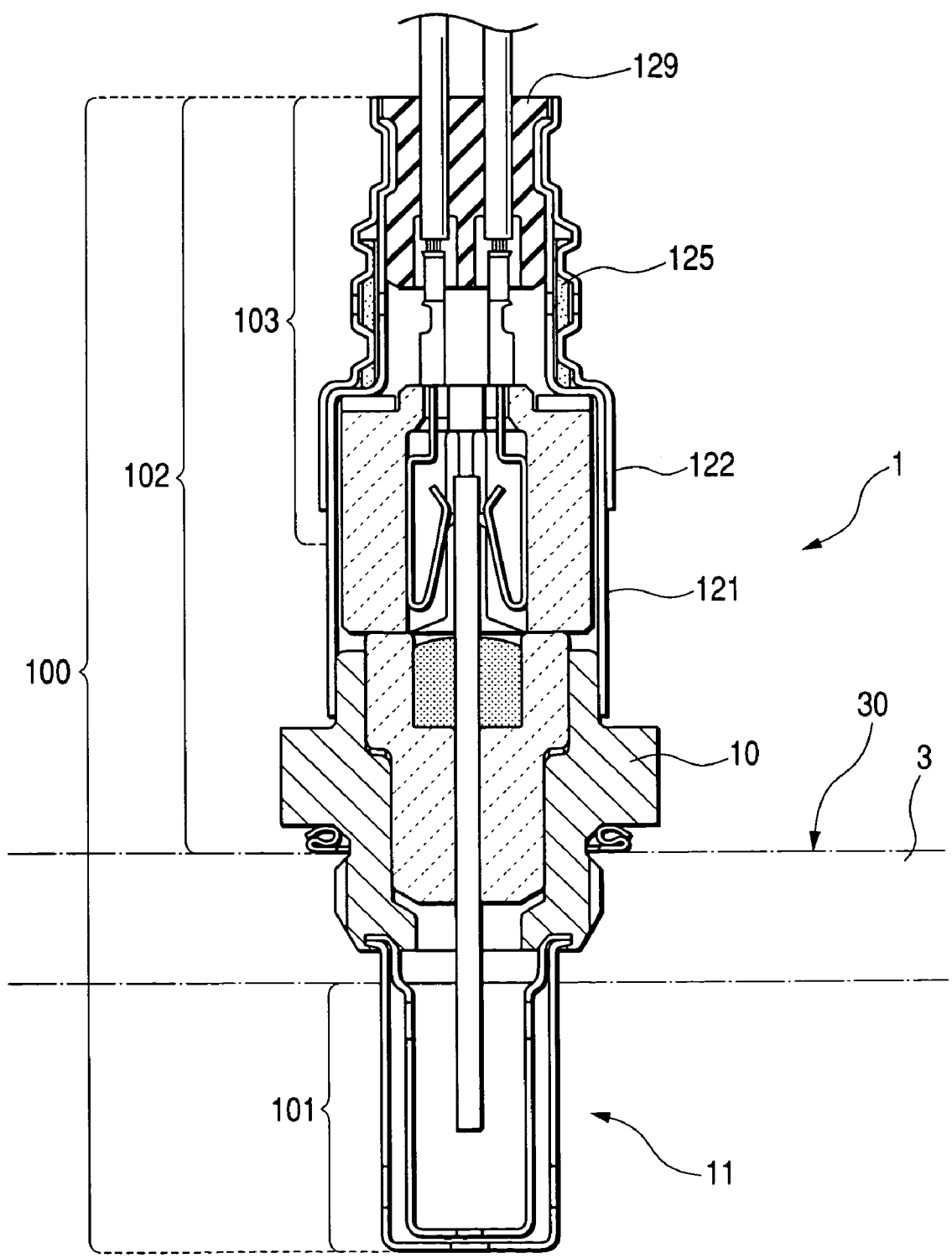
FIG. 3 is an axially cross-sectional view showing another construction of the gas sensor according to the first embodiment.

In addition, as shown in FIG. 3, it is also possible to further lengthen the outer cover 122 provided outside the atmospheric side cover 121.

Still additionally, as shown in FIG. 3, even if, without setting the emissivity of the entire atmosphere 102 at 0.3 and less, the emissivity of a region shown as a range 103 is set to be equal to or lower than 0.3 and the emissivity of portions other than this region exceeds 0.3, the effects of this embodiment are also obtainable.

The range of this region has a length of 0.6H or more from the base end portion of the gas sensor 1 along the axial direction of the gas sensor 1, where H represents the length of the atmosphere surface 102 along the axial direction thereof.

In the gas sensor 1 according to this embodiment, the portions sensitive to heat are the elastic insulating member 129 for hermetically sealing the base end portion of the atmospheric side cover 121 and the water repelling filter 125. As mentioned above, the elastic insulating member 129 is disposed at the base end portion of the atmospheric side cover 121 and the water repelling filter 125 is basically disposed in the base end of the gas sensor 1 because the atmosphere is introduced at the position thereof (first embodiment). Therefore, a region whose emissivity is 0.3 or less is made to range from the base end portion to a position corresponding to a distance of 0.6 H or more, thereby particularly preventing the temperature rise in the vicinity of the base end portion of the gas sensor 1 and protecting the elastic insulating member 129 and the water repelling filter 125.

Second Embodiment

According to this embodiment, in the gas sensor with the construction according to the first embodiment, the emissivity of the atmosphere surface or the area of the region whose emissivity is low is changed and the temperature rise suppression effect are measured.

A sample 0 is a reference sample in which a passive-state film is formed on the atmosphere surface without forming a shot-blast-treated surface and the metallic shiny slightly appears but the emissivity of the atmosphere surface is as high as 0.4.

The atmosphere surface of a sample 1 does not have formed passive-state film, and the metallic shiny of SUS 310 directly appears.

On the atmosphere surface of a sample 3, a passive-state film is sufficiently formed by heating.

The atmosphere surface of a sample 2 has a treated surface formed by shot-blast-treating an atmosphere surface which is in the state of the sample 3.

In each of gas sensors based on the samples 1 to 3, the emissivity of the entire region from a base end portion of the atmosphere surface to a top portion thereof is set at a predetermined value.

In each of gas sensors based on samples 4 to 6, the emissivity of a predetermined region in the atmosphere surface is set at 0.3. That is, in the case of the sample 4, the range from the base end portion of the atmosphere surface to a position corresponding to a distance of 0.7H is shot-blast-treated while the sample 5 is shot-blast-treated over the range from the base end portion thereof to a position corresponding to a distance of 0.6H and further the sample 6 is shot-blast-treated over a range from the base end portion thereof to a position corresponding to a distance of 0.5H.

For the measurement of the emissivity of the atmosphere surface of each of these samples, the reflectance thereof is measured through the use of a spectroradiometer covering the visible light and near-infrared light, put on the market. Since the transmission of the electromagnetic wave does not occur in the atmosphere surface, the emissivity=1—the reflectance.

Secondly, a description will be given hereinbelow of a method of measuring a temperature of a gas sensor.

Figure 4:
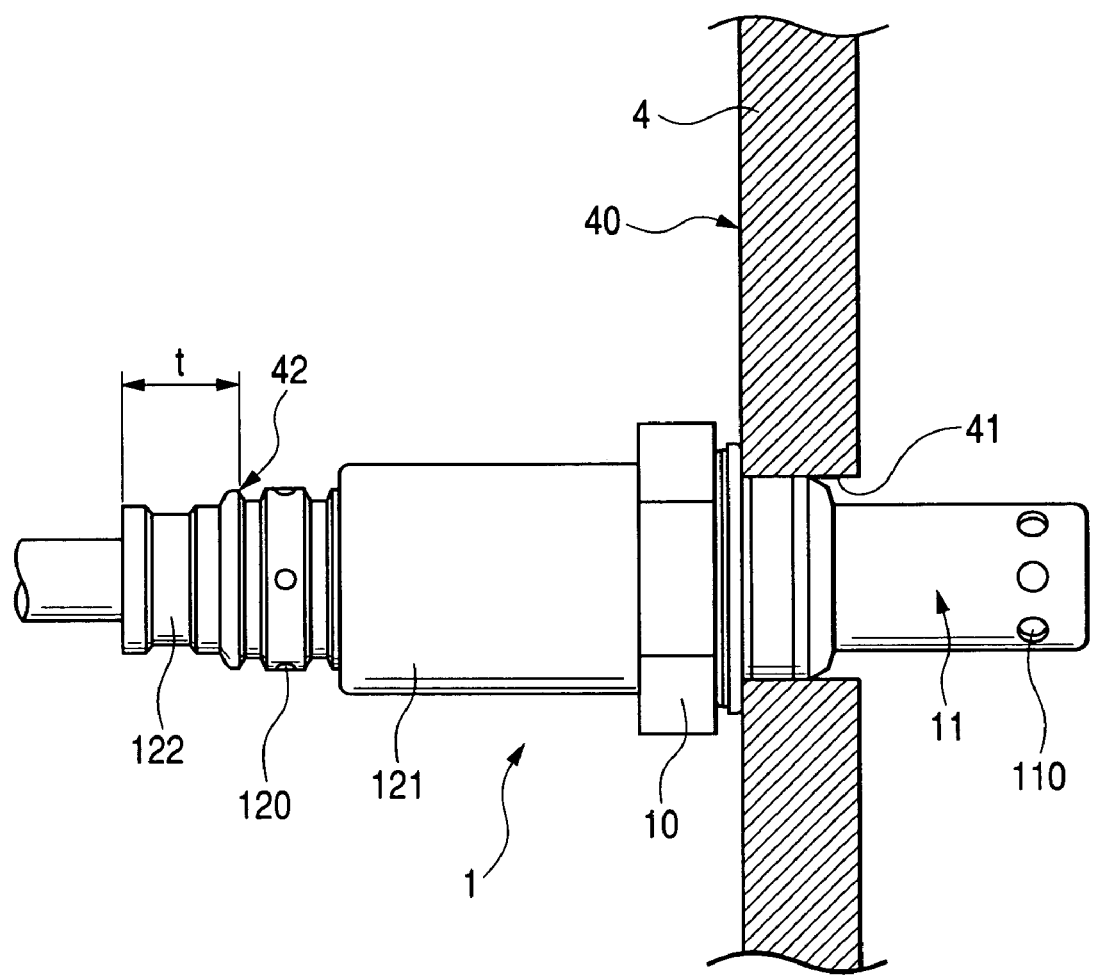
FIG. 4 is an illustration useful for explaining a method of measuring temperatures of portions of a gas sensor according to a second embodiment of the present invention.

As shown in FIG. 4, a gas sensor 1 is inserted into a fixing hole 41 of a mounting tool 4. The tool 4 is heated until the temperature of a tool surface 40 reaches 800° C. In this state, after the elapse of 30 minutes within which the temperature of a temperature measuring position 42 comes into a stable condition, the temperature was measured through the use of a thermocouple attached onto the temperature measuring position 42. The temperature measuring position 42 is a position separated by t=10 mm from the base end portion of the gas sensor 1.

In inserting the gas sensor 1, as in the case of the actual use, the measured gas surface is positioned on the right side in the illustration while the atmosphere surface is positioned on the left side in the illustration.

With a value measured on the sample 0 being used as a reference value, the temperature differences relative to this reference value are shown in the following table 1.

TABLE 1

| Sample | State of Atmosphere Surface | Emissivity | Range | Temp. Difference | Evaluation |
|---|---|---|---|---|---|
| 0 | brown to dark brown by heating, shiny | 0.4 | H | Ref. | — |
| 1 | base surface of SUS310 | 0.15 | H | −25° C. | A |
| 2 | shot-blasted surface of SUS310 | 0.3 | H | −18° C. | A |
| 3 | brown by heating, shiny | 0.35 | H | −5° C. | C |
| 4 | shot-blasted surface of SUS310 | 0.3 | 0.7H | −14° C. | A |
| 5 | shot-blasted surface of SUS310 | 0.3 | 0.6H | −11° C. | A |
| 6 | shot-blasted surface of SUS310 | 0.3 | 0.5H | −8° C. | B |

In this table 1, when the temperature difference is equal to or smaller than 5° C., the evaluation reference is marked with "C", and when the temperature difference is larger than 5° C. but smaller than 10° C., the evaluation reference is marked with "B", and when the temperature difference is equal to or larger than 10° C., the evaluation reference is marked with "A".

As obvious from the table 1, it was found from the samples 1 to 3 that, when the emissivity is equal to or lower than 0.3, a high temperature reduction effect is obtainable.

Moreover, it was found from the samples 4 to 6 that, when a region in which the emissivity is equal to or lower than 0.3 is provided over a range from a base end portion of the gas sensor to a position corresponding to a distance of 0.6H or more, a higher temperature reduction effect is attainable.

It should be understood that the present invention is not limited to the above-described embodiment, and that it is intended to cover all changes and modifications of the embodiments of the invention herein which do not constitute departures from the spirit and scope of the invention.

What is claimed is:

1. A gas sensor internally including a sensing element for measuring a specific gas concentration in a measured gas to be measured, an outer surface of said gas sensor including a measured gas surface exposed to said measured gas and an atmosphere surface exposed to the atmosphere, and at least a portion of said atmosphere surface has an emissivity equal to or lower than 0.3; wherein a region of said atmosphere surface, which contributes 60% or more of said atmosphere surface, has an emissivity equal to or lower than 0.3.

2. The sensor according to claim 1, wherein at least a portion of said atmosphere surface has an emissivity equal to or lower than 0.15.

3. The sensor according to claim 1, wherein said emissivity is a value with respect to an electromagnet wave having a wavelength of 0.5 to 1 μm.

4. The sensor according to claim 1, wherein said atmosphere surface comprising a shot-blast-treated surface.

5. A gas sensor internally including a sensing element for measuring a specific gas concentration in a measured gas to be measured, an outer surface of said gas sensor including a measured as surface exposed to said measured gas and an atmosphere surface exposed to the atmosphere and at least a portion of said atmosphere surface has an emissivity equal to or lower than 0.3;

wherein, when a distance from a base end portion of said atmosphere surface to a top portion thereof in an axial direction of said gas sensor is taken as H, said emissivity is set to be equal to or lower than 0.3 in a region corresponding to a distance of 0.6H or more from said base end portion thereof toward said top portion in said axial direction.

6. The sensor according to claim 5 wherein at least a portion of said atmosphere surface has an emissivity equal to or lower than 0.15.

7. The sensor according to claim 5 wherein said emissivity is a value with respect to an electromagnetic wave having a wavelength of 0.5 to 1 μm.

8. The sensor according to claim 5 wherein said atmosphere surface comprising a shot-blast-treated surface.

* * * * *